United States Patent [19]
Abbate et al.

[11] Patent Number: 5,747,693
[45] Date of Patent: May 5, 1998

[54] SYSTEM FOR TAKING TRANSVERSE MEASUREMENTS

[75] Inventors: Agostino Abbate, Clifton Park; Julius Frankel, Renssalaer; Mark Doxbeck, Troy, all of N.Y.

[73] Assignee: The United States of America as represented by the Secretary of the Army, Washington, D.C.

[21] Appl. No.: 707,362

[22] Filed: Sep. 4, 1996

Related U.S. Application Data

[63] Continuation-in-part of Ser. No. 540,617, Oct. 25, 1995, abandoned, which is a continuation of Ser. No. 373,126, Jan. 17, 1995, abandoned, which is a continuation of Ser. No. 972,340, Nov. 6, 1992, abandoned.

[51] Int. Cl.$^6$ ............................................. G01N 29/10
[52] U.S. Cl. .................... 73/622; 73/644; 83/522.26; 72/31.02; 29/407.07; 29/407.01
[58] Field of Search ..................... 73/622, 623, 584, 73/587, 644, 638; 29/407.01, 407.05, 407.07; 72/31.01, 31.02; 83/522.26

[56] References Cited

U.S. PATENT DOCUMENTS

| | | | |
|---|---|---|---|
| 3,782,228 | 1/1974 | Lindemann et al. | 73/622 |
| 3,896,662 | 7/1975 | Camp et al. | 73/622 |
| 4,114,456 | 9/1978 | Dory | 73/622 |
| 4,358,945 | 11/1982 | Pärtzel | 73/584 |
| 4,976,149 | 12/1990 | Ichikawa et al. | 73/622 |
| 5,063,779 | 11/1991 | Landry et al. | 73/622 |
| 5,097,881 | 3/1992 | Mack | 73/622 |

*Primary Examiner*—Hezron E. Williams
*Assistant Examiner*—Nashmiya Ashraf
*Attorney, Agent, or Firm*—John F. Moran; Michael C. Sachs

[57] ABSTRACT

A system can take transverse measurements of an elongated workpiece. The system has a base for holding the workpiece oriented in an axial direction. A carriage mounted on the base can move axially. This carriage has a linear measurement device for providing a linear signal signifying the axial position of the carriage. An ultrasonic assembly is mounted on the carriage, and includes a nozzle for projecting a stream of liquid against the workpiece. This ultrasonic assembly also has an ultrasonic transducer for transmitting an ultrasonic wave into the stream and for detecting an ultrasonic wave returning in the stream. This ultrasonic transducer has a transducer terminal for exchanging signals signifying the occurrence of ultrasonic waves transmitted into and returning from the stream. A control device is coupled to the transducer terminal for (a) exchanging signals with the ultrasonic transducer, (b) initiating transmission of an ultrasonic wave into the stream, and (c) receiving a signal signifying the return of ultrasonic waves in the stream. This control device can provide a sense signal signifying the operation of the ultrasonic assembly. The system also has a signal processor coupled to the carriage and the control device for providing in response to the linear signal and the sense signal, an evaluation signal signifying the straightness of the workpiece.

17 Claims, 3 Drawing Sheets

5,747,693

SYSTEM FOR TAKING TRANSVERSE MEASUREMENTS

This application is a continuation-in-part of application Ser. No. 08/540,617 filed Oct. 25, 1995, now abandoned which is a continuation of Ser. No. 08/373,126 filed Jan. 17, 1995, now abandoned which itself continues from Ser. No. 07/972,340 filed Nov. 6, 1992, also now abandoned the entire file wrapper contents of which applications are herewith incorporated by reference as though fully set forth herein at length.

GOVERNMENT INTEREST

The invention described herein may be made, used, or licensed by or for the U.S. Government without payment to us of any royalty thereon.

BACKGROUND OF THE INVENTION

1. Field of the Invention

The present invention relates to measurement systems and, in particular, to systems for taking transverse measurements with an ultrasonic wave in a liquid stream.

2. Description of Related Art

Commercially available "squirters" employ a nozzle for projecting a liquid stream against the surface of a unit to be measured. The squirter includes an ultra-ultrasonic transducer working with ultrasonic frequencies in the order of megahertz, for examples Commercially available pulser/receivers can establish the carrier frequency and modulation of the ultrasonic wave in the stream. Such external equipment can control the squirter and provide instrumentation for measuring the timing between the initiating pulse and the echoes. The ultrasonic wave may be pulse modulated so that the return time of echos indicates the distance to a surface or discontinuity within the unit being measured. For example, an ultrasonic wave impinging perpendicularly an a flat plate will return an echo for both the front and back surfaces of the plate.

The manufacture of gun barrels is an exacting art wherein extreme care should be taken to ensure the straightness of the barrel. Lack of straightness can affect the accuracy of the gun. During manufacture, especially while the gun barrel is being machined on the inside diameter, it is important to know the concentricity of the outside surface to the inside diameter or bore of the tube, as well as the straightness of the bore. Evidence shows the effectiveness or lethality of the gun barrel is affected by bore straightness.

Straightness is checked at various stages of manufacturing; if necessary, the tube is taken to a press where it is straightened by three point bending. This process may need to be repeated several times and in different planes.

In the manufacture of a gun barrel, a rough forging initially receives autofrettage and thermal treatment and then it is placed in a straightening press. Before using the straightening press, the amount and the direction of the required straightening must be determined. Straightness has been measured in various ways.

A conventional method is to place a string from one end of the barrel to the other. A "mouse" is used to measure any bowing or cresting of the barrel. Equivalently, the string can be replaced with a laser beam and the bowing and cresting observed similarly. Such measurements are impossible when the barrel is being machined, and therefore the tube has to be placed on an appropriate stand.

In one known technique a laser is mounted on a cylindrical plug that is passed through the gun barrel. Variations in the exit angle of the beam are measured as a function of axial barrel position. This process has inherent limits in that slight cocking of the plug carrying the laser can adversely affect the measurement. Furthermore, such a measurement can only be performed with a stationary barrel.

Another optical method involves the use of a laser to measure the distance via interferometry, or the use of an optical intensity sensor. With the latter, light is reflected off the tube surface and the sensor measures the intensity received, which is also distant dependent.

The "mouse" technique uses an electromagnetic device to produce a magnetic field that is coupled across an air gap to the metal of the workpiece. In this case, the workpiece can be rotated and the spacing between the workpiece and the electromagnetic device will change to change the impedance of the electro-magnetic device. This impedance change can be measured electrically and correlated to the magnetic gap, thereby measuring distance. None of these systems, however, are appropriate for measuring during machining the displacement of the inside wall of a hollow piece such as a gun tube.

A classical method of measuring the surface of a gun barrel is to use a mechanical probe having a dial. This probe can be passed along the outside and inside surface of the gun to measure concentricity. With this technique, however, the probe is not readable when inside the gun tube during machining.

Another disadvantage with such measurement systems is that the gun barrel, which may be seventeen or more feet long, must have its straightness checked in a separate fixture. Thus the gun barrel must be removed from one of the stages where the actual manufacturing process is occurring and carried to a fixture just to measure straightness.

Accordingly, there is a need for an improved measurement device that can check straightness in a simple and effective manner without unnecessary transportation of a workpiece.

SUMMARY OF THE INVENTION

In accordance with the illustrative embodiments demonstrating features and advantages of the present invention, there is provided a system for taking transverse measurements of an elongated workpiece. The system includes a base for holding the workpiece oriented in an axial direction. A carriage mounted at the base can impart axial motion. This carriage has a linear means for providing a linear signal signifying the axial position of the carriage. The system also includes an ultrasonic assembly mounted on the carriage. The ultrasonic assembly has a stream means for projecting a stream of liquid against the workpiece, as well as an ultrasonic transducer means for transmitting an ultrasonic wave into the stream and detecting an ultrasonic wave returning in the stream. This ultrasonic transducer means has a transducer terminal for exchanging signals signifying the occurrence of ultrasonic waves transmitted into and returning from the stream. Also included is a control means coupled to the transducer terminal for: (a) exchanging signals with the ultrasonic transducer means, (b) initiating transmission of an ultrasonic wave into the stream, and (c) receiving a signal signifying return of ultrasonic waves in the stream. This control means can provide a sense signal signifying the operation of the ultrasonic assembly. The system also includes a signal processing means coupled to the carriage and the control means for providing in response to the linear signal and the sense signal, an evaluation signal signifying the dimensioning of the workpiece.

In accordance with a related method of the same invention, transverse measurements are taken of an elongated workpiece. The method includes the step of holding the workpiece oriented in an axial direction. Another step is projecting a stream of liquid against the workpiece. The method also includes the step of transmitting an ultrasonic wave into the stream and detecting an ultrasonic wave returning in said stream. Another step is displacing the stream axially. Another step is evaluating the dimensioning of the workpiece by examining along the axis of the workpiece, variations of echoes in the ultrasonic wave.

By employing apparatus and methods of the foregoing type, improved measurements can be taken of an elongated workpiece. By employing such apparatus or equipment, preferably, a computerized ultrasonic squirter system can display wall thickness variations, alignment of the center axis of the gun tube with the rotational axis of the machining lathe and gun tube straightness. All of these measurements can be obtained in real time without interfering with the machining or boring of the gun tube.

In the preferred embodiment, an elongated workpiece is mounted in a base and is rotated substantially about the axis of the workpiece. A squirter is mounted on a carriage to move axially. The squirter preferably projects a stream radially against the outside surface of the workpiece. Echoes from ultrasonic waves induced in the stream enable measurement of the relative position of the outside the workpiece and its internal bore.

By rotating the workpiece, the echolocation pattern indicates the relative position of the outside and inside surface of a workpiece such as a gun barrel, as a function of axial and radial position. This information can be processed by various control devices and displayed by a computer. For example, the computer can produce a display showing the transverse silhouette of the barrel, illustrating its offset from the ideal center. Alternatively, an axial plot of displacement from true straightness can be displayed. In still other embodiments, the computer can determine whether the straightness or other dimensions have gone beyond tolerance, so that a warning is given, the process is stopped and/or shaping tools can be adjusted.

BRIEF DESCRIPTION OF THE DRAWINGS

The above brief description as well as other objects, features and advantages of the present invention will be more fully appreciated by reference to the following detailed description of presently preferred, but nonetheless illustrative embodiments, in accordance with the present invention, when taken in conjunction with the accompanying drawings, wherein.

DETAILED DESCRIPTION OF THE PREFERRED EMBODIMENTS

Figure 1:
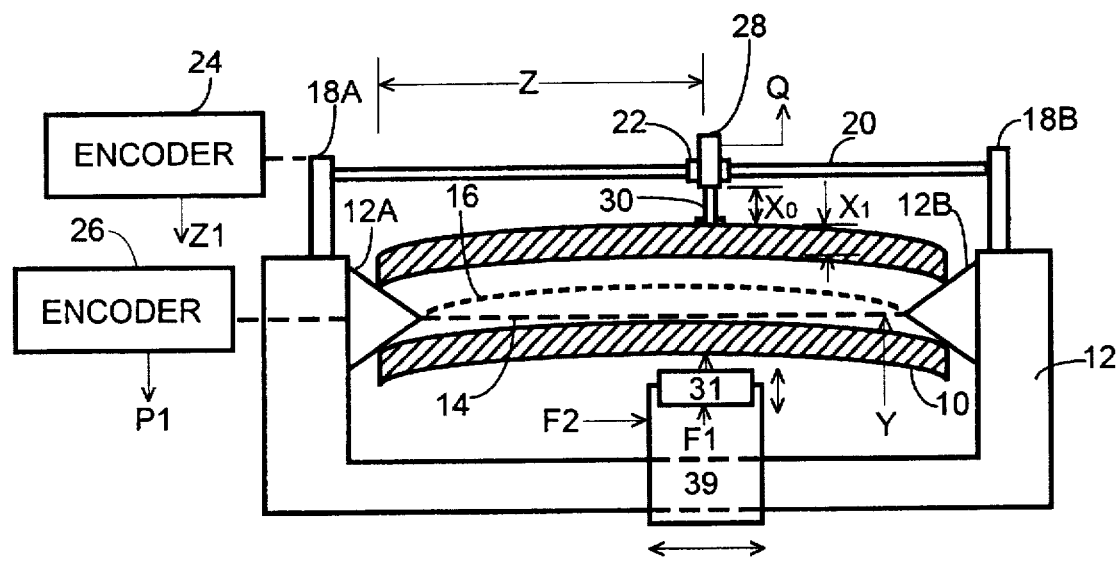
FIG. 1 is a schematic, elevational view of a measurement system and method in accordance with the principles of the present invention.

Referring to FIG. 1, that system is measuring a workpiece 10, illustrated herein as a gun barrel having essentially a cylindrical outside and inside surface, although frustroconical and other shapes are contemplated. For example, a solid shaft or other elongated workpiece can be subjected to measurement. Workpiece 10 is shown having a coaxial bore that is not straight and follows an exaggerated curved axis 16. Base 12 is shown having a pair of opposing mandrels 12A and 12B designed to fit onto workpiece 10 and turn it on a predetermined axis of rotation 14. Base 12 can be structured much like a lathe, although in some embodiments a simple fixture can be used and no rotation imparted at all.

Stanchions 18A and 18B are supporting a carriage, illustrated herein as a lead screw 20. Lead screw 20 supports a carrier 22, that incorporates a nut that rides on lead screw 20. The nut is fixedly attached to be on carrier 22. Lead screw 20 can be turned by a motor (not shown) or manually, to move carrier 22 axially, that is, in a direction parallel to axis 14.

The rotation of lead screw 20 is measured by a linear means 24, shown herein as a carriage shaft encoder. Shaft encoder 24 can be any one of various commercially available encoders. Encoder 24 can provide a pulse at regular, angular increments as well as a specialized pulse on another line when the shaft completes 360 degrees of rotation. The output of encoder 24 is provided on line Z1. A similar base shaft encoder 26 is shown mechanically coupled to mandrel 12A to provide a digital signal on terminal P1, also indicating the angular rotation of workpiece 10 within base 12.

An ultrasonic assembly 28 is shown mounted on carrier 22 to move axially therewith. The ultrasonic assembly 28 is shown projecting radially against the outside surface of workpiece 10 a stream 30 of cutting fluid, water, or other liquid. The pump and nozzle (not shown) within or associated with assembly 28 that creates stream 30 is herein referred to as a stream means. Ultrasonic assembly 28 also includes an ultrasonic transducer means for generating an ultrasonic wave of about, but not necessarily, 5 MHz which propagates along stream 30 and reflects back at various interface in workpiece 10 to produce echoes.

Assembly 28 is commercially available and is often called a "squirter." For example, a type HAX600 squirter can be purchased from the Harrisonic unit of Staveley Sensors, Inc. of East Hartford, Conn. Similar squirters can be purchased from other suppliers such as Panametrics, Inc. of Waltham, Mass. Assembly 28 is a relatively compact unit typically in a package 4 inches long and one inch in diameter. The output of ultrasonic assembly 28 is identified as transducer terminal Q. The squirter can be specified by identifying its carrier frequency (in this example, 5 MHz) and focal length. The focal length is nominally the depth to which the echoes penetrate. For example, in the example of FIG. 1 echoes can be reflected from the outside surface of workpiece 10 as well as the inside surface of the axial bore. Thus in the example of FIG. 1, the focal length would be the length of the stream 30 ($X_0$) plus the thickness ($X_1$) of the wall of workpiece 10. However a flat or unfocussed transducer can also be used.

Assembly 28 has the capacity to provide a stream ¼ inch in diameter, but basically the stream dimensions are sufficient to provide a continuous, steady stream with sufficient capacity to carry the energy of the ultrasonic waves propagating therethrough. Preferably, the stream falls vertically to minimize the pressure demanded from the pump of assembly 28. The pump supplying stream 30 can be an external pump (not shown) with sufficient capacity and pressure to produce a steady stream that does not have bubbles or pump-induced vibrations.

In other embodiments where the workpiece 10 is not rotated, the ultrasonic assembly 28 can be mounted on an orbiting carriage (not shown) to orbit axis 14 and make circumferentially spaced measurements.

In the example of FIG. 1, workpiece 10 is shown with a highly exaggerated deflection between straight axis 14 and bore axis 16. In most practical situations such bending would make the workpiece unsalvageable. Nevertheless, this exaggeration is shown for illustrative purposes.

Workpiece 10 is shaped by an axially moveable means 31, shown herein as a cutting tool working the outside surface of workpiece 10. Tool 31 is connected to a mechanism 39 that can move tool 31 axially (or radially) with respect to the workpiece. In this embodiment, the axial and radial motion of tool 31 can be controlled by feedback signals applied along lines F1 and F2, respectively.

As described hereinafter, the deviation from straightness can be sensed by the measurement equipment to cause tool 31 to reshape the workpiece and thereby in effect to straighten it. Cutting tool 3 1 moves along axis 14 of the lathe 12 while the gun barrel 10 is rotating. Adjustment of tool 31 is, intended to encompass all useful adjustments. For example, the principal cutting parameters which affect results are the depth of the cutting and both the angular and linear speeds of the lathe. Usually both speeds are constant during a single pass and are varied for the following one, but it is also possible to modify the cutting parameters after each measurement.

Figure 2:
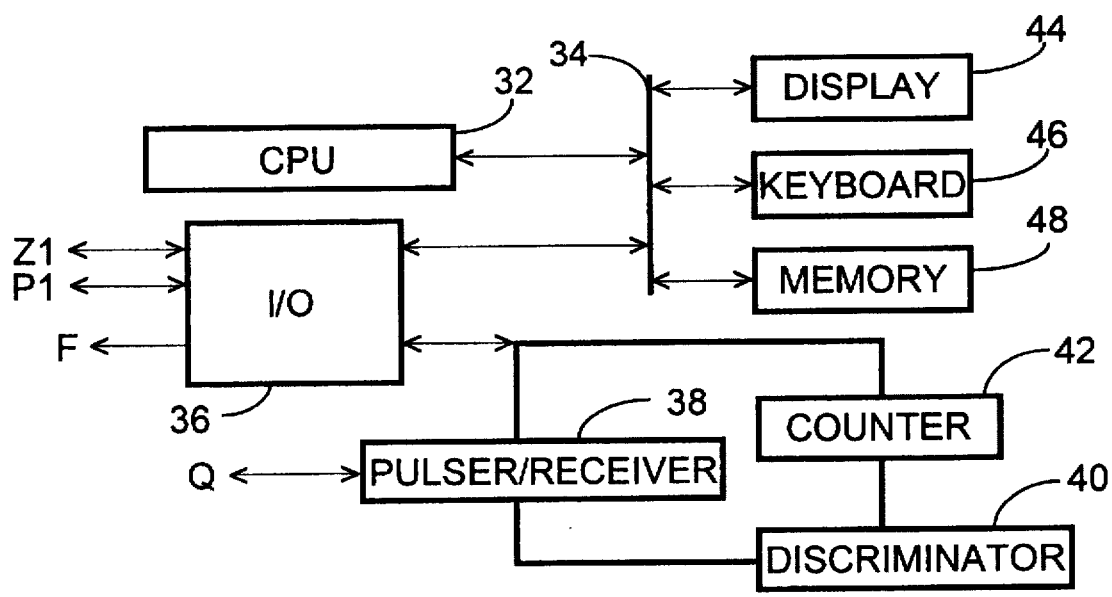
FIG. 2 is a schematic block diagram of a control means and signal processing means that cooperates with the system of FIG. 1.

Referring to FIG. 2, a signal processing means 32 is shown herein as a desk top computer such as a Hewlett Packard, type 382 basic controller, although general purpose computers and other types of mini- and micro-processors can be employed instead. Processor 32 is shown connected through a bus 34 to an input/output device 36. In this embodiment, various digital to analog and analog to digital converters can be employed to receive asynchronous digital or analog signals and convert them into signals that are conveyed synchronously along bus 34. In this embodiment, the input/output device 36 employs a data acquisition board for receiving such data. An additional board, a GP-IB type board, employs standard communications protocols. Input/output device 36 is shown exchanging data with lines Z1, P1 and F, previously illustrated in FIG. 1.

Input/output device 36 is also shown receiving inputs from a control means, which, in this embodiment, is a commercially available pulser/receiver 38, for example, a pulser/receiver type MBS8000 from Matec Corporation of Hopkington, Mass. The particular model selected will depend upon the nature of the signals produced by the above mentioned squirter as well as the desired accuracy of measurement. Other manufacturers of suitable pulser/receivers include Panametrics Inc. of Waltham, Mass. The digital output of unit 38 is applied to input/output device 36 and indicates the return time of various echoes sensed by unit 38.

Pulser/receiver 38 is shown connecting through previously mentioned line Q (to ultrasonic assembly 28 of FIG. 1). Accordingly, unit 38 can establish the carrier frequency and the modulation thereof. In this embodiment, the carrier is set at 5 MHz and the modulation is pulse amplitude modulation, although pulse frequency, pulse phase shift, and other forms of modulation could be used instead. The pulse repetition rate is set at 10 kHz. Essentially, the carrier frequency and pulse repetition rate is selected to ensure adequate accuracy of the measurement and to avoid an interference between returning echoes and new initiating pulses. Pulse width is, suitably, 100 microseconds. The sound wave can also be generated using a pulsed generator; in this case a high voltage short pulse is applied to the transducer.

A discriminator 40 cooperates with unit 38. Discriminator 40 receives pulses detected by unit 38 and reacts to crossing of a threshold that is approximately 80% of the average peak of the pulses. In one embodiment unit 48 is a type 584 CF, constant fraction discriminator manufactured by EG & G Ortec, of Oakridge, Tenn., although other discriminators can be employed instead. When a pulse exceeds this threshold, discriminator 40 supplies a signal to counter 42. Counter 42 may be a Hewlett Packard type 5370B universal time interval counter. Counter 42 measures the time intervals between ultrasonic echoes. These intervals are compared with measurements from standards of known thickness and thus transformed into spatial measurements. Counter 42 thereby produces a count that is set by the time between pulses from discriminator 40. The count thus accumulated by counter 42 is supplied as an input to input/output device 36.

Processor 32 is connected to a display means 44, preferably a conventional CRT. Also connected to processor 32 is a keyboard 46 to be used in the usual fashion. Connected to processor 32 through bus 34 is memory 48. Memory 48 can include various types of memory including: volatile random access memory, nonvolatile read only memory, disk memory (hard and soft), tape drives, CD ROM's, and various other types of memory sources. Processor 32 is programed by virtue of software residing in memory 48. The operation of such software will be described hereinafter.

To facilitate an understanding of the principles associated with the foregoing apparatus, its operation will be briefly described in connection with the fabrication of a gun barrel, although the principles equally apply to workpieces of different types and shapes.

A roughly forged, cast or machined workpiece such as a gun barrel 10 has the general shape of a hollow cylinder with a coaxial bore. After initial shaping such as forging, the gun barrel can be subjected to well known processes such as autofrettage and thermal treatment before being measured for straightness. The device can then be mounted between the mandrels 12A and 12B of base 12 to be machined and initially measured for straightness. Base 12 can rotate workpiece 10 much like a lathe.

It is important to note that the machining of the outside diameter of the gun barrel can be performed simultaneously with the straightness measurement. This is a significant savings in the amount of handling. Ordinarily, the barrel would be machined and then removed to a separate measuring station, a considerable effort for a seventeen foot barrel. Instead, measurements can be made during the machining process with the added advantage of providing an opportunity to adjust the machining process to account for bowing or other defects in the gun barrel.

Figure 3:
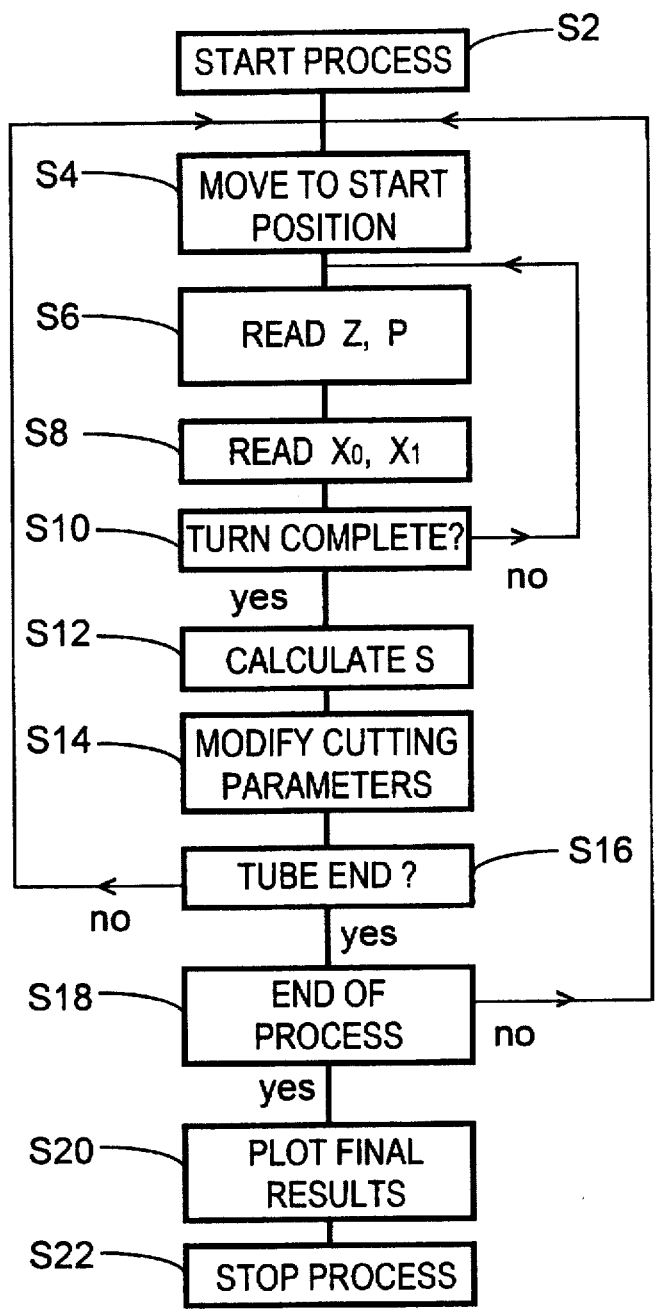
FIG. 3 is a flowchart illustrating the operation of software associated with the central processing unit of FIG. 2.

An operator can use keyboard 46 (FIG. 2) to command the beginning of the process. Commands thus applied along bus 34 are received by processor 32, which initiates a program contained in memory 48. In step S2 (FIG. 3) of the program the process is started. In this situation, commands are forward along lines Q to ultrasonic assembly 28 to set its various operating parameters. Similarly, various state variables are set in pulser/receiver 38 (FIG. 2) and counter 42. Consequently, ultrasonic assembly 28 will operate with the various operating parameters described above.

Next in step S4, conditions are established for bringing various mechanisms to their starting positions. This can either be a signal telling the operator to manually reposition the unit or a control signal can be sent to a servomotor (not shown) to turn lead screw 20 and bring carrier 22 to one side, for example, to the left in FIG. 1. This motion is equivalent to reducing variable Z (FIG. 1) to a reference value.

The resulting motion of carrier 22 along lead screw 20 is measured by shaft encoder 24, which produces a signal along line Z1 that is recorded by processor 32. Verification that carrier 22 has reached its start position can be obtained from the operator giving keyboard confirmation or by limit switches (not shown).

Also, the need to start rotation of workpiece 10 can be announced through display 44 and a motor circuit can be closed either manually or through a relay (not shown) automatically operated through input/output device 36, to begin rotation of workpiece 10. As workpiece 10 rotates, shaft encoder 26 supplies angular rotation data along line PI to input/output device 36.

In step S6 (FIG. 3) processor 32 reads data from input/output device 36, namely, the signals provided along lines Z1 and P1. This data is an indication of the axial position Z (FIG. 1) of carrier 22 and ultrasonic assembly 28 as well as the angular rotation of workpiece 10.

Next in step S8 processor 32 measures the data provided by pulser/receiver 38 and counter 42. As noted before, these devices provide essentially timing information indicating the timing of pulses reflected from the outside and inside surface of workpiece 10. Essentially, the first returning pulse has a timing corresponding to dimension $X_0$. The second returning pulse has a timing corresponding to the dimension $X_0$ plus $X_1$. For thin walls, the resonance frequency method can be used instead.

Then, in step S10 processor 32 determines whether workpiece 10 has completed a full revolution. This full revolution can be determined by counting the pulses from encoder 26 (FIG. 1) or by awaiting an indexing mark from the encoder produced once per revolution. If a complete revolution has not occurred steps S6 and S8 are repeated. In this way, the computer assembles a number of data sets, each consisting of angular information, radial information and axial position.

Once a full turn is completed, control passes to step S12, wherein processor 32 calculates variable S.

Figure 4:
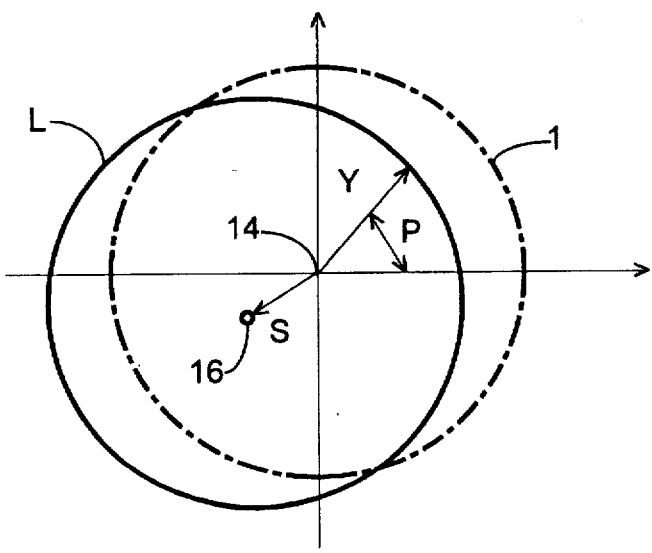
FIG. 4 is a diagram of a possible computer display, indicating the locus of measurements relative to an ideal locus.

Variable S is graphically illustrated in FIG. 4, the two dimensional plot of the position of the inside surface of workpiece 10. The origin of the plot of FIG. 4 coincides with the axis of rotation 14 of FIG. 1. Dimension Y corresponds to the spacing between axis 14 and the inside surface of workpiece 10.

Since the axis 14 is at a constant spacing from ultrasonic assembly 28 the following $X_0+X_1+Y$ is constant. Thus Y is simply obtained by subtracting $X_0$ and $X_1$ from a constant. Since each Y is obtained in set of data including the angular position P workpiece 10, Y is easily plotted to show the locus L, of the inside surface. Effectively, the center of the locus of Y is bore axis 16.

Using well understood analysis techniques, computer 32 can determine the displacement S between axes 14 and 16. For example, the processor can try hypothetical circles with the data set to find a match that is within a predetermined tolerance. Locus L should be compared to the ideal locus I, an ideally straight gun tube wherein the center of the bore coincides with the axis of rotation. While the locus L of the inside surface of workpiece 10 is shown, the same analysis could be provided for the outside surface of the workpiece.

The thus calculated displacement values are stored along with its corresponding axial position in step S12. Thereafter in step S14 the magnitude of displacement is analyzed. If necessary, the shaping of workpiece 10 can be affected. Accordingly, processor 32 can issue an adjustment signal along data line F from input/output device 36. This signal can be a command for a servo-motor (not shown) to adjust cutting tool 31 so that the tool can shape the workpiece appropriately. In extreme cases, the shaping process can be stopped.

Thereafter in step S16 processor 32 evaluates the variable Z. If the end of the workpiece 10 has not been reached, steps S4–S14 are repeated, thereby assembling a new set of radial measurements as a function of angular position at another axial position.

Eventually, the end of the gun tube will be reached as determined by measuring the rotations indicated by encoder 24 (FIG. 1). At that time, in step S18, computer processor 32 will inquire whether the process is finished. The manufacturing operation may require a repeat of the process, for example, multiple passes of a cutting tool where much material must be machined from a barrel. Otherwise, step S20 is executed.

Figure 5:
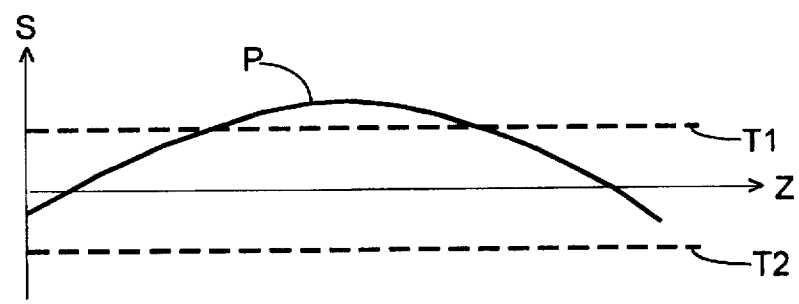
FIG. 5 is an alternate display showing displacement from straightness as a function of axial position.

In step S20, the displacement variable S described before in connection with FIG. 4 can be plotted as shown in FIG. 5 as a function P of axial displacement Z. As shown in FIG. 5, the tolerance limits T1 and T2 can be shown on a CRT display 44 (FIG. 2) and against plot P of the variable S. The deviation of the workpiece shows that tolerance T1 is exceeded near the center of the workpiece. Once this plot is displayed the process ends at step S22.

An advantage herein is that subsequent straightening step can be avoided should the measurements made above show that the gun barrel is within tolerance. If residual bowing that could not be corrected by the machining itself persists, this bowing can be corrected in a press. Since the nature of the bowing of the workpiece has already been determined, the gun barrel can then be brought directly to a straightening press of a conventional design. Knowing the position and the angular orientation of the bowing, the barrel can be properly positioned in the straightening press to impart a compensating bend.

Thereafter the outer surface of the gun barrel can be machined again and its straightness again checked as described above, before placing the barrel again in a straightening press. The inside of the barrel can then be bored to make the bore concentric. The boring can be performed simultaneously with the measurement process just described. Afterward the gun tube may be swaged and thermally treated and its straightness again determined in the manner described.

Several more rounds of machining and straightening can now be performed before subjecting the barrel to a final straightness check using perhaps an alternate, but highly accurate technique, such as a laser measurement. Thereafter the barrel can be finished, honed and rifled in the usual fashion.

It is to be appreciated that various modifications may be implemented with respect to the above described preferred embodiments. While the machining of a gun barrel was described in other embodiments a shaft or other elongated workpiece can be checked for straightness. The present equipment can be used to measure the straightness of any hollow or solid shaft as a jet engine rotor or generator shaft, statically or dynamically while being machined. Furthermore some of the programing steps can be supplemented, condensed, eliminated or reordered depending upon the application. Also depending upon the desired accuracy, the pulser/receiver can be of various types and the discriminator and counter can be eliminated in instances where high accuracy is unnecessary. A constant fraction discriminator is necessary for applications requiring resolutions of better than 100th of an inch. Furthermore, the angular position of the workpiece and the linear position of the squirter can be determined with various alternate measurement devices. Additionally, the display provided by the computer can be augmented to show relations between the outside diameter and the inside diameter as a function of circumferential position or axial position and may be displayed as a table, bar chart, or otherwise.

Obviously, many modifications and variations of the present invention are possible in light of the above teachings. It is therefore to be understood that within the scope of the appended claims, the invention may be practiced otherwise than as specifically described.

What is claimed is:

1. A system for taking transverse measurements of a gun barrel with a coaxial bore, and for machining a cylindrical outer surface of said gun barrel while monitoring straightness and wall thickness, comprising;
    base means for rotatably holding said gun barrel;
    mandrel means operatively connected to said base means for rotating said gun barrel about a predetermined axis of rotation;
    carriage means operatively attached to said base means for linearly moving said carriage means parallel to said predetermined axis of rotation;
    linear shaft encoder means for providing a linear signal indicating the position of said carriage means relative to said base means;
    base shaft encoder means operatively coupled to said mandrel means for providing a digital signal indicating the angular rotation of said gun barrel;
    ultrasonic assembly means operatively mounted on said carriage means and which linearly moves with said carriage and which comprises;
        (a) stream means for projecting a stream of liquid against said cylindrical outer surface of said gun barrel;
        (b) ultrasonic transducer means for transmitting an ultrasonic wave into said stream of liquid and for detecting an ultrasonic wave returning in said stream of liquid, said ultrasonic transducer means having a transducer terminal for exchanging signals signifying the occurrence of ultrasonic waves transmitted into and returning from said stream;
    tool support means horizontally slideably positioned on said base means operatively for holding a tool for machining said gun barrel in response to signals received from said ultrasonic transducer means;
        control means electrically coupled to said transducer terminal for (a) exchanging signals with said ultrasonic transducer means, (b) initiating transmission of an ultrasonic wave into said stream, and (c) receiving a signal signifying return of ultrasonic waves in said stream, said control means being operable to provide a sense signal signifying the operation of said ultrasonic assembly means; and signal processing means electrically coupled to said carriage means and said control means for providing in response to said linear signal from said linear shaft encoder means and said sense signal, an evaluation signal signifying the dimensioning of said gun barrel.

2. A system according to claim 1 wherein said wherein said stream means is operable to direct said stream radially against said cylindrical outer surface.

3. A system according to claim 2 wherein said evaluation signal of said signal processing means is composed to signify relative eccentricity of the outer surface of said gun barrel with said coaxial bore.

4. A system according to claim 2 wherein said evaluation signal of said signal processing means is composed to signify position of said coaxial bore relative to said predetermined axis of rotation.

5. A system according to claim 4 wherein said evaluation signal of said signal processing means includes means to signify the position of said coaxial bore relative to said base means at a plurality of positions along said cylindrical outer surface of said gun barrel.

6. A system according to claim 1 further comprising; feedback means for controlling the movement of said tool support means in response to said evaluation signal.

7. A system according to claim 6 wherein said feedback means is operable to stop said tool support means movement in response to said evaluation signal exceeding a predetermined tolerance.

8. A system according to claim 5 wherein said signal processing means is operable in response to said sense signal to determine the center of said coaxial bore, said system comprising:
    display means for graphically displaying the magnitude of displacement of the center of said coaxial bore from the predetermined axis of rotation for a plurality of axial positions on said gun barrel.

9. A system according to claim 5 wherein said signal processing means is operable in response to said sense signal to provide a warning signal in response to said gun barrel being less straight than a predetermined standard.

10. A system according to claim 1 wherein said signal processing means operatively stops the rotation of said mandrel means and said gun barrel when said sense signal indicates said gun barrel is less straight than a predetermined standard, so that said tool means can be adjusted.

11. A system according to claim 5 wherein said carriage means comprises;
    a pair of stanchions operatively supported by said base means; a lead screw rotatively supported intermediate said stanchions;
    a carrier threadedly connected to said lead screw for operatively supporting said ultrasonic assembly means thereon, said carrier moving parallel to said predetermined axis of rotation when said lead screw is rotated.

12. A system according to claim 5 wherein, said signal processing means being coupled to said base shaft encoder to compose said evaluation signal as a function of said digital signal.

13. A system according to claim 1 wherein said ultrasonic transducer means operates with a pulse modulated carrier frequency, said carrier frequency being above audible.

14. A system according to claim 13 wherein said carrier frequency is at least five hundred kilohertz and the pulse modulation has a repetition frequency not exceeding ten kilohertz.

15. A system according to claim 13 wherein said control means comprises:
    a discriminator for producing a pulse in response to the returning ultrasonic wave having a peak amplitude exceeding a given threshold.

16. A system according to claim 15 wherein said given threshold is approximately given by a fixed percentage of the peak amplitude of the returning ultrasonic wave.

17. A system according to claim 1 wherein said tool support means is moveable in a direction perpendicular to said cylindrical outer surface of said gun barrel for ultimately shaping said cylindrical outer surface of said gun barrel.

* * * * *